United States Patent [19]

Knell

[11] Patent Number: 5,756,815
[45] Date of Patent: May 26, 1998

[54] PROCESS FOR THE PREPARATION ARYLAMALONATES

[75] Inventor: Marcus Knell, Ingelheim, Germany

[73] Assignee: American Cyanamid Company, Madison, N.J.

[21] Appl. No.: 820,268

[22] Filed: Mar. 18, 1997

[51] Int. Cl.[6] .................................................. C07C 69/76
[52] U.S. Cl. ........................ 560/82; 560/83; 560/105; 546/184
[58] Field of Search ..................... 560/82, 83, 105; 546/184

[56] References Cited

FOREIGN PATENT DOCUMENTS

| 0 550 113 A2 | 12/1991 | European Pat. Off. ...... C07D 487/04 |
| WO 94/20501 | 3/1993 | WIPO ........................ C07D 487/04 |

*Primary Examiner*—Gary Geist
*Assistant Examiner*—Rosalynd Keys

[57] ABSTRACT

A process for the preparation of dialkyl arylmalonates of formula I,

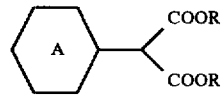

comprises treating an arylmethlhalide of formula II

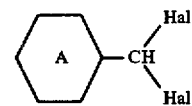

with magnesium in an inert solvent, and a dialkyl carbonate or an alkyl chloroformate. A and R are as defined. The process is useful in the preparation of intermediate agro or pharmaceutical chemicals, or liquid crystals.

11 Claims, No Drawings

PROCESS FOR THE PREPARATION ARYLAMALONATES

BACKGROUND OF THE INVENTION

Arylmalonates are useful as intermediates for the preparation of a variety of compounds which are useful as agrochemicals, pharmaceuticals or liquid crystals. In particular, they are key intermediates in the preparation of fungicidal 6-aryltriazolopyrimidines which are described for example in EP 0 550 113 and WO 94/20501.

Conventionally the preparation of these compounds is carried in a 4-step synthesis starting from arylmethylhalides according to the following reaction scheme:

Scheme 1

Conventional process for the preparation of arylmalonates:

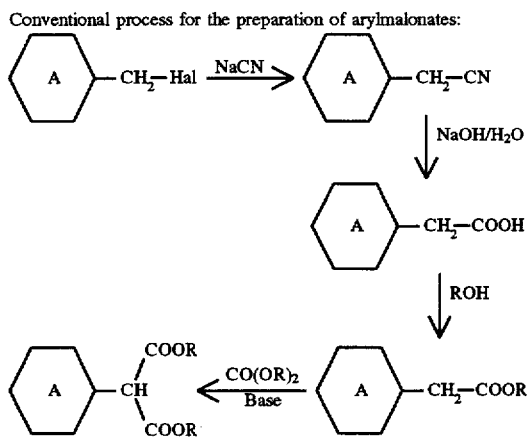

However, this method is not entirely satisfactory for large scale production, since highly toxic sodium cyanide is required and the overall yield of the reactions starting from arylmethylhalide is often low.

SUMMARY OF THE INVENTION

The present invention provides an effective and efficient process for the preparatoin of dialkyl arylmalonates of formula I,

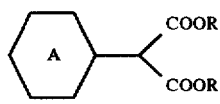 (I)

wherein ring A is an optionally substituted, optionally benzo-condensed phenyl group or an optionally substituted nitrogen containing 6-membered heteroaromatic group, and R represents alkyl, which comprises treating an arylmethyidihaide of formula II

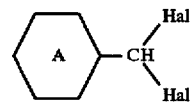 (II)

wherein ring A has the meaning given for formula I, and

Hal represents halogen, with at least two moles magnesium related to 1 mole of arylmethyldihalide of formula II, in an inert solvent, and with at least two moles of a dialkyl carbonate or an alkyl chloroformiate, in particular a dialkyl carbonate, related to 1 mole of arylmethyldihalide of formula II.

It is, therefore, an object of the present invention to provide an efficient new process for the preparation of arylmalonates. efficient new process for the preparation of arylmalonates.

Other objects and advantages of the present invention will be apparent to those skilled in the art from the following description and the appended claims.

DETAILED DESCRIPTION OF THE PREFERRED EMBODIMENTS

In general terms, unless otherwise stated, as used herein the term halogen atom may denote a bromine, iodine, chlorine or fluorine atom, and is especially a bromine or chlorine atom.

Optionally substituted moieties may be unsubstituted or have from one up to the maximal possible number of substituents. Typically, 0 to 2 substituents are present.

In general terms, unless otherwise stated herein, the term alkyl as used herein with respect to a radical or moiety refer to a straight or branched chain radical or moiety. As a rule, such radicals have up to 10, in particular up to 6 carbon atoms. Suitably an alkyl moiety has from 1 to 6 carbon atoms, preferably from I to 3 carbon atoms. A preferred alkyl moiety is a methyl or especially an ethyl group.

In general terms, unless otherwise stated herein, the term optionally substituted or optionally benzo-condensed phenyl, as used herein with respect to a radical or moiety refers to an aryi group having 6 or 10 carbon atoms, preferably 6 carbon atoms, in particular phenyl being optionally substituted by one or more halogen atoms, nitro, cyano, alkyl, preferably $C_{1-6}$ alkyl, alkoxy, preferably $C_{1-6}$ alkoxy.

In general terms, unless otherwise stated herein, the term heteroaromatic group, as used herein with respect to a radical or moiety refers to a heteroaryl group having 6 ring atoms selected from carbon, nitrogen, oxygen and sulphur, at least one of which being nitrogen.

In a preferred embodiment

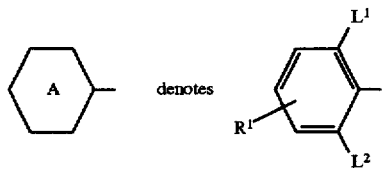

in which $L^1$ and $L^2$ each independently represent a halogen atom, preferably fluorine or chlorine, and $R^1$ represent a hydrogen or halogen atrm or an alkyl or alkoxy group.

In a particularly preferred embodiment ring A represents 2-chloro-6-fluorophenyl.

Further preferred embodiments of the process according to the present invention is a process wherein:

the magnesium used is activated with I 2-dibromoethane (DBE) or diethylether (DEE);

1 mole of arylmethyldihalide of formula II is treated with 2.1 to 5.0, preferably 2.2 to 4.2 moles magnesium;

a mixture comprising the arylmethyidihalide of formula II, the dialkyl carbonate or the alkyl chioroformiate and optionally an inert solvent is added preferably slowly dosed, to a mixture comprising magnesium and an inert solvent;

the reaction is carried out in the presence of an inert solvent selected from the group consisting of diethylether (DEE), diisopropylether, tert-butylmethylether (TBME), dimethoxymethane (DMM), 2,2-dimethoxypropane (DMP), diethoxyethane, tetrahydrofuran (THF), tetrahydropyran (THP), toluene, glyme, pyridine, tri-n-butylamine (TBA), TMEDA and mesitylene, or a mixture of these solvents;

the reaction is carried out at temperatures between 0° C. and 100° C., preferably between 50° C. and 95° C.;

1 mole of arylmethyidihalide of formula II is treated with 3 to 12 moles of the dialkyl carbonate or 3 to 12 moles of the alkyl chloroformiate;

the reaction mixture obtained by reacting the compound of formula II with magnesium and the dialkyl carbonate or the alkyl chloroformiate is treated with a base;

the reaction mixture obtained by reacting the compound of formula II with magnesium and the dialkyl carbonate or the alkyl chloroformiate is heated until the products have been completely dissolved and is transferred to a mixture comprising the base and the dialkyl carbonate or the alkyl chloroformiate;

the base is an alkali metal alkoxide, the reaction mixture is heated up to 150° C. upon adding the base.

As a rule, the initiation of the Grignard formation requires a long time in solvents like THF or DMM, therefore activation with DEE or DBE yields more reproducible results. Preferably a mixture of the arylmethyldihalide and a solvent is slowly added to a mixture of magnesium, a solvent and 0.005 to 0.02 moi of the activator related to 1 mole of the arylmethyldihalide.

Since, as a rule, an excess of magnesium is used, the remaining magnesium can be used as activ bottom in the following reaction without further activation.

Most preferred the reaction of is carried out in mixtures of solvents and or activators, in particular in mixtures essentially consisting of:

THF or DMM and DBE or DEE, as rule 1000 parts of THF or DMM to 0.5–2.0 parts or DBE; or toluene, DEE and TBA.

During the reaction with the dialkylcarbonates it is favorable to avoid that an excess of the free Grignard reagent is present, wherein Ar is a halogenated phenyl group, in order to prevent a Wurtz-type side reaction according to reaction scheme 2:

Scheme 2 Wurtz-type reaction:

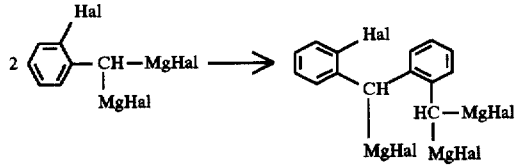

Therefore, the Grigrnard reagent is prefearbly generated in-situ in the presence of the dialkyl carbonate or the alkyl chloroformiate which are 5 used in excess. In a particularly preferred embodiment a mixture of the arylmethyidihalide and the dialkyl carbonate, preferably diethyl carbonate, is added to a mixture of the magnesium, the inert solvent, in particular THF, and the activator, in particular DBE.

As a rule the reaction between the Grignard reagent and the dialkyl 10 carbonate or the alkyl chloroformiate is carried out at elevated temperatures, preferably between 0° C. and 100° C/, in particular between 50° C. and 95° C., most preferred between 60° C. and 85° C.

In order to reduce the formation of an arylacetate as a side-product, the reaction is preferably carried out in the presence of a base, most preferred the reaction mixture obtained by the reaction of the Grignard reagent and the dialkyl carbonate or the alkyl chloroformiate is treated with a base.

However, the desired product can be obtained in high yields even without post-treatment with a base.

The reaction mixture is preferably added to the base upon heating to temperatures above 100° C. At this temperature; the reaction mixture becomes a colored clear solution and can be easily transferred to a solution which essentially consists of the base, optionally an inert solvent and/or a dialkyl carbonate.

Preferred bases are metal alkoxides, in particular sodium alkoxides as for example sodium methoxide, sodium ethoxide or sodium tert-butoxide.

After addition to the base the reaction mixture is, as a rule, heated up to 150° C., preferably to 110° C.–135° C. most preferred to about 120° C., and the alkariol formed from the dialkyl carboxylate is distilled off, The surplus dialkyl carbonate is preferably distilled off under reduced pressure.

The remaining reaction mixture preferably is neutralized with diluted acid, the phases are separated and the organic layer is dried and concentrated.

The crude product obtained can be purified according to standard methods for example by distillation in vacuo, chromatographic methods or crystallization.

However, the crude prduct obtained according to the process of this invention is pure enough to be used as intermediate without further purification.

The reaction is as a rule completed within 0.2 to 50, in particular 0.4 to 40 hours.

In order to facilitate a further understanding of the invention, the following illustrative examples are presented. The invention is not limited to the specific embodiments described or illustrated, but encompasses the full scope of the appended claims.

EXAMPLE 1

Preparation of diethyl 2-chloro-6-fluorophenylmalonate

A mixture of magnesium (3.4 g), THF (5 ml) and dibromoethane (0.1 ml) is heated to 75° C. under stirring. After 5 minutes a mixture of 2-chloro-6-fluorobenzaldichloride (10 g), diethylcarbonate (45 ml) and THF (20 ml) is dosed over a period of 1 hours. The reaction mixture is heated to 75° to 80° C. and stirred for 1 hour. The reaction mixture is separated off from un-reacted magnesium. The solvent is distilled off under reduced pressure. Upon diluting with toluene 5(50 ml) and cooling down to 20° C. the reaction mixture is neutralized with a mixture of concentrated HCI (250 ml) and water (40 ml). The phases are separated and the organic phase is dried with magnesium sulfate and concentrated in vacuo to yield the crude 5 product (70 % yield), which is purified by distillation under reduced pressure. The obtained product shows the following properties:

bp: 115° C. at 0.1 mbar $^1$H-NMR (DMSO, 300 MHz):

δ (ppm)=7.45 (m, 2H), 7.30 (m, 1H), 5.22 (s, 1H), 4.19 (q7 4H), 1.18 (t, 6H)

EXAMPLES 2 TO 10

Preparation of dialkyl 2-chloro-6-fluorophenylmalonate

Analogously to example 1 2-chloro-6-fluorobenzaldichloride (BAG) is treated with magnesium, a carbonyiation reagent in different solvents and at different temperatures.

The relative amounts of the reactants and solvents, the reaction temperature of the carbonylation step and yields are shown in table I in which the following abbreviations have been used:

| | |
|---|---|
| DBE | 1,2-dibromothane |
| THF | tetrahydrofuran |
| DEC | diethylcarbonate |
| DMM | dimethoxymethane |
| THP | tetrahydropyran |
| DEE | diethylether |
| DMP | 2,2-dimethoxypropane |
| DIP | diisopropylether |
| TBME | tert-butylmethylether |
| TBA | tri-n-butylamine |
| DMC | dimethylcarbonate |

TABLE I

Examples 2 to 10

| Example | Initiator | Solvent | Mg/BAC | Cabonylation agent | Cabonylation agent/BAC | temperature (°C.) | Time (hrs) | Yield (%) |
|---|---|---|---|---|---|---|---|---|
| 2 | DBE | THF | 3 | DEC | 10 | 65–85 | 0.5 | 61 |
| 3 | DBE | THP | 3 | DEC | 8 | 80 | 54 | 64 |
| 4 | DBE | DMM | 3 | DEC | 6 | 55 | 16 | 55 |
| 5 | DBE/DEE | DMP | 3 | DEC | 4 | 85 | 60 | 26 |
| 6 | DBE/DEE | DIP | 4 | DEC | 4 | 75 | 42 | 65 |
| 7 | DBE/DEE | TBME | 4 | DEC | 4 | 70 | 42 | 60 |
| 8 | DBE/DEE | pyridine | 3 | DEC | 4 | 65 | 20 | 17 |
| 9 | DBE | THF/TBA | 3 | DEC | 2 | 85 | 1 | 22 |
| 10 | DBE | THF | 3 | DMC | 10 | 60–62 | 0.5 | 32 |

EXAMPLE 11

Preparation of diethyl 2-chlora-6-fluorophenylmalonate

A mixture of magnesium (17 g), THF (75 ml) and dibromoethane (0.5 ml) is heated to 75° C. under stirring. After 5 minutes a mixture of 2-chloro-6-fluorobenzaldichloride (50 g) and diethylcarbonate (280 ml) is dosed over a period of 2 hours. The reaction mixture is heated to 75° to 80° C. and stirred for 1 hour. Upon heating to 100° C. the reaction mixture is transferred to a mixture of sodium ethylate (6.4 g) and diethylcarboxylate (90 ml). The resulting mixture is heated to 125° C. and stirred for 12 hours. Further sodium ethylate (38.4 g) is added to the reaction mixture. The surplus diethylcarbonate is distilled of under reduced pressure (105° C., 250 mbar). Upon diluting with toluene (200 nl.) and cooling down to 20° C. the reaction mixture is neutralized with a mixture of concentrated HCl (110 ml) and water (200 ml). The phases are separated and the organic phase is dried with magnesium sulfate and concentrated in vacuo to yield the crude product (61 g/81% yield).

What is claimed is:

1. A process for the preparation of dialkyi arylmalonates of formula I,

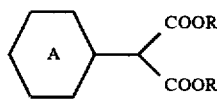

wherein ring a is an optionally substituted, optionally benzo-condensed phenyl 6 group or an optionally substituted nitrogen containing 6-membered heteroaromatic group, and R represents alkyl, which comprises treating an arylmethyidihalide of formula II

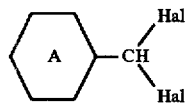

wherein ring A has the meaning given or formula I, and

Hal represents halogen, with at least two moles of magnesium related to 1 mole of the arylmethyidihalide of formula II, in an inert solvent and with at least two moles of dialkyl carbonate or an alkyi chloroformiate related to 1 mole of the arylmethyldihalide of formula II.

2. A process according to claim 1, wherein the magnesium used is activated with 1,2-dibromoethane and/or diethylether.

3. A process according to claim 1, wherein 1 mole of arylmethyldihalide of formula II is treated with 2.1 to 5.0 moles magnesium.

4. A process according to claim 1, wherein a mixture comprising the arylmethydihalide of formula II, the dialkyl carbonate or the alkyl chloroformiate and optionally an inert solvent is added to a mixture comprising magnesium and arn inert solvent.

5. A process according to claim 4, wherein the reaction is carried out in the presence of an inert solvent selected from the group consisting of diethyether, disopropylether, tert-butylmethylether, dimethoxymethane, 2,2-dimethoxypropane, diethoxyethane, tetrahydrofuran, tetrahydropyran, toluene, glyme, pyridine, TMEDA and mesitylene, or a mixture of these solvents.

6. A process according to claim 1, wherein the reaction is carried out at temperatures between 0° C. and 100° C.

7. A process according to claim 1, wherein 1 mole of arylmethyidihalide of formula II is treated with 3 to 12 moles of the dialkyi carbonate or 3 to 12 moles of the alkyl chloroformiate.

8. A process according to claim 1, wherein the reaction mixture obtained by reacting the compound of formula II with magnesium and the dialkyl carbonate or the alkyl chioroformiate is treated with a base.

9. A process according to claim 8, wherein the reaction mixture obtained by reacting the compound of formula II with magnesium and the dialkyl carbonate or the alkyl chloroformiate is heated until the products have been completely dissolved and is transferred to a mixture comprising the base and the dialkyl carbonate or the alkyl chloroformiate.

10. A process according to claim 8 or 9, wherein the base is an alkali metal alkoxide.

11. A process according to claim 1, wherein the reaction mixture is heated up to 150° C. upon adding the base.

* * * * *